United States Patent [19]
Agrawal et al.

[11] Patent Number: 5,741,329
[45] Date of Patent: Apr. 21, 1998

[54] METHOD OF CONTROLLING THE PH IN THE VICINITY OF BIODEGRADABLE IMPLANTS

[75] Inventors: Chandra Mauli Agrawal; Kyriacos A. Athanasiou, both of San Antonio, Tex.

[73] Assignee: Board of Regents, The University of Texas System, Austin, Tex.

[21] Appl. No.: 361,332

[22] Filed: Dec. 21, 1994

[51] Int. Cl.$^6$ ........................................ A61F 2/02
[52] U.S. Cl. ................ 623/11; 623/16; 606/76; 523/113; 523/115; 424/423
[58] Field of Search .................. 623/11, 16; 606/76, 606/77; 523/113, 115; 424/423, 426

[56] References Cited

U.S. PATENT DOCUMENTS

| | | | |
|---|---|---|---|
| 3,911,098 | 10/1975 | Capozza | 424/428 |
| 4,479,911 | 10/1984 | Fong | 264/4 |
| 4,645,503 | 2/1987 | Lin et al. | 623/16 |
| 4,694,039 | 9/1987 | Mottus et al. | 524/718 |
| 4,722,948 | 2/1988 | Sonderson | 523/115 |
| 4,990,161 | 2/1991 | Kampner | 623/16 |
| 5,286,763 | 2/1994 | Gerhart et al. | 604/40 |
| 5,433,751 | 7/1995 | Christel et al. | 606/77 |

FOREIGN PATENT DOCUMENTS

| | | |
|---|---|---|
| 0 50 939 A | 9/1991 | European Pat. Off. |
| 0 564 369 A1 | 6/1993 | European Pat. Off. |

OTHER PUBLICATIONS

Acuna, V. et al., "Composites of Lactic Acid Polymer and Calcium Phosphate or Calcium Carbonate as Degradable Bone Fillers," Advances in Biomaterials, 10. Biomaterial Tissue Interfaces, 1992, pp. 391–398.

DeGroot, K., "Medical Applications of Calciumphosphate Bioceramics," J. Ceramic Society of Japan, International Edition, vol. 99, No. 10, Oct. 1991, JP, pp. 917–926.

Saalfeld, U. et al., "Solubility Behaviour of Synthetic Hydroxyapatites in Aqueous Solution: Influence of Aorphous Constituents on pH Value," Biomaterials (Sep. 1994) 15(11):905–908.

Daniels, A. U. et al., "Toxicity of Absorbable Polymers Proposed for Fracture Fixation Devices," 38th Ann. Meeting, Orthopaedic Res. Soc., Feb. 17–20, 1992, Washington, D.C., p. 88.

Allemann et al., "In vitro Extended–release Properties of Drug–loaded Poly (DL–lactic acid) Nanoparticles Produced by a Salting–out Procedure," Pharm. Res. (1993) 10:12.

Bostman et al., "Biodegradable Internal Fixation for Malleolar Fractures," J. Bone Surgery (1987) 69–B:615–619.

(List continued on next page.)

Primary Examiner—Paul Prebilic
Attorney, Agent, or Firm—Greenlee, Winner and Sullivan, P.C.

[57] ABSTRACT

The invention discloses pH-controlling devices that comprise a biodegradable polymer and a pH-controlling substance, particularly an alkaline, acidic or buffering agent. By way of example, such alkaline agents include calcium carbonate and sodium bicarbonate. Methods of preparing such devices are also described. Methods for enhancing biocompatibility of an implantable device are also provided, as neutralizing alkaline materials are released at a rate that offsets changes in pH typically observed as polymers degrade to various acidic or alkaline by-products. By way of example, biodegradable polymers include PLA, PGA, polycaprolactone, copolymers thereof, or mixtures thereof. A new technique is also disclosed to increase the surface porosity of porous implants which have a tendency to form relatively impermeable coverings. This technique entails the use of mechanical means to remove at least part of said covering, thus increasing the implant's surface porosity and permeability.

19 Claims, 5 Drawing Sheets

PLA-PGA Implant with Base

Degradation ⟶ Acidic Products + Basic Products ⟶ pH prevented from decreasing significantly

OTHER PUBLICATIONS

Freed et al., "Joint Resurfacing Using Allograft Chondrocytes and Synthetic Biodegradable Polymer Scaffolds," J. Biomed. Mat. Res. (1994) 28:891–899.

Freed et al., "Biodegradable Polymer Scaffolds for Tissue Engineering," Biotechnology (Jul. 1994) 12.

Gilding and Reed, "Biodegradable polymers for use in surgery–polyglycolic/poly (lactic acid) homo–and copolymers," Polymer (1979) 20:1459–1464.

Mariette et al., "Release of the GRF29NH$_2$ Analog of Human GRF44NH2 from a PLA/GA Matrix," J. Control Release (1993) 24(1–3):237–246.

Suganuma, J. and Alexander, H., "Biological Response of Intramedullary Bone to Poly–L–Lactic Acid," J. Appl. Biomaterials (1993) 4:13–27.

Taylor et al., "Six Bioadsorbable Polymers: In Vitro Acute Toxicity of Accumulated Degradation Products," J. Appl. Bio. Materials (1994) 5:151–157.

Tencer et al., "Bone Ingrowth into Polymer Coated Porous Synthetic Coralline Hydroxyapatite," IEEE/Engineering in Med. and Biol. Soc., Annual Conference (1986) pp. 1668–1671.

Vasenius et al., "Do Intramedullary Rods of Self–Reinforced Poly–L–lactide or Poly–DL/L–lactide Cause Lactic Acid Acidosis in Rabbits?", Clin. Mater. (1992) 10(4);213–218.

Younes et al., "Biodegradable PELA Block Copolymers: In Vitro Degradation and Tissue Reaction," Biomater. Artif. Cells Artif. Organs (1988) 1604):705–719.

METHOD OF CONTROLLING THE PH IN THE VICINITY OF BIODEGRADABLE IMPLANTS

FIELD OF THE INVENTION

The field of the present invention relates to implantable devices. The invention also relates to the field of methods for controlling pH, particularly through the use of implantable devices that regulate the surrounding pH. Methods for preparing an implantable device are also related to the field of the present invention. Additional methods for enhancing the biocompatibility of an implantable device are also disclosed.

BACKGROUND OF THE INVENTION

Biodegradable polymers, such as those belonging to the family of polylactic acid (PLA) and polyglycolic acid (PGA), are widely used for fabricating implantable devices. Such devices are currently used for drug delivery, joint resurfacing (using allograft chondrocytes and synthetic polymer scaffolds), and fracture fixation in medicine, particularly in the fields of orthopaedics, podiatry and maxillofacial surgery. The degradation of these materials has been studied both in vivo and in vitro. It has been reported that they degrade primarily by hydrolysis of ester bonds. Upon degradation, these materials release acidic by-products, which then enter the tricarboxylic acid cycle and are reduced to carbon dioxide and water.

Basic substances, such as calcium carbonate and hydroxyapatite, have been described to some extent in the literature in a variety of applications. For example, Kampner describes a permanent joint prosthesis having a biodegradable anchor of glycolic acid and polylactic acid polyesters with calcium carbonate and hydroxyapatite. The Fong et al. patent[5] employs sodium hydroxide in microspheres, the sodium hydroxide providing for the regulation of microsphere core material release. The Kampner patent[6] refers to hydroxyapatite in polymeric bone implants, and Allmann et al.[7] refers to enhancing drug loading efficiency of PLA nanoparticles by using a savoxepine base and modifying the pH of an aqueous base. Basic substances thus have been used to increase drug loading efficiency or to increase the solubility of an active ingredient.

Several studies have reported on the effects of pH change during biodegradable polymer breakdown. For example, Younes et al.[8] reports a relatively greater polymer mass loss with increasing pH.

Other investigators in the area of biodegradable implantable materials have raised questions about the biocompatibility and toxicity of biodegradable polymer breakdown products[1-3]. For example, Bostman et al. reported aseptic sinus formation with biodegradable implants used to repair fractures in humans. Lowered pH in the vicinity of an implantable device from breakdown of PLA and PGA breakdown has also been suggested to cause adverse effects like inflammation and tissue damage[2,3]. However, changes in pH that occur in vivo with polymer implant degradation have not been reported to significantly affect physiological levels of blood components. For example, Vasenius et al.[10] report "normal" results for blood components and acid base balance in vivo with implanted rods of the biodegradable polymers poly lactic acid or poly D, L lactic acid.

Solving the problem of controlling pH shifts due to polymer breakdown products would improve the biocompatibility of a variety of implantable devices for both short term and long term use in the medical industry. A method for controlling pH would also be useful in other industries where pH changes from polymer degradation present a problem.

SUMMARY OF THE INVENTION

The above and other needs are met in the disclosed devices.

Many of the problems associated with shifts in pH due to biodegradable polymer breakdown products are in part remedied by the compositions and methods of the present invention. The inventors have found that the inclusion of a pH regulating substance, such as an alkaline substance, an acidic substance, or a buffering agent, included with the biodegradable polymer, will hinder shifts in pH that typically occur as the polymer breaks down. By including a pH-controlling material with the polymer itself, the life of the device may also be prolonged. This technique will also guard against a variety of pH-related in vivo side effects associated with pH shifts at implantation sites. These advantages and others are realized according to the various compositions and methods provided in the present invention.

It is also contemplated that the implantable devices of the invention having a pH-regulating material may be used as scaffolds for joint resurfacing. In this aspect, primary or passaged cells, such as mesenchymal stem cells or chondrocytes, are cultured on discs of biodegradable polymer scaffolds that include a pH-controlling substance. Such scaffolds can have the form of nonwoven mesh of PGA fibers 12 to 14 μm in diameter, with the mesh being 0.1 to 0.2 cm thick, a bulk density of 55–65 mg/cm$^3$ and a void volume of 92–96%. The resulting scaffold may be used as an implant. Techniques for preparation and use of polymer scaffolds, which do not contain pH regulating substances of this invention, are described in Freed et al., "Joint Resurfacing Using Allograft Chondrocytes and Synthetic Biodegradable Polymer Scaffolds," *Journal of Biomedical Materials Research*, Vol. 28, 891–899 (1994) and Freed et al., Biodegradable Polymer Scaffolds for Tissue Engineering," *Biotechnology*, Vol. 12, (July, 1994), incorporated herein by reference.

Another aspect of the invention provides a method for minimizing tissue damage related to adverse pH changes from the presence of polymer breakdown products. Still another aspect of the invention provide a technique for enhancing implant biocompatibility. Because a pH controlling agent, such as an alkaline, acidic, or buffering substance, is included with the polymer, it is released at a rate that is proportional to the rate at which the polymer degrades. Potential changes in pH, such as from increases in acidity related to break down of polylactic or polyglycolic acid, may thus be offset by the release of an alkaline substance included with the polymer.

In another aspect, the invention provides a method for inhibiting sudden pH shifts surrounding a biodegradable polymer implant. By way of example, one particular embodiment of the method comprises preparing a mixture of a pH controlling substance and a biodegradable polymer, forming an implantable device with the mixture, and placing the device in contact with an environment that will degrade the biodegradable polymer. One example of such an environment would be that surrounding the implant of the device after implantation in the tissue of an animal.

The pH regulating effects of the invention may also be realized by placing the device in contact with a culture of cells or in a biological fluid. Because the pH-controlling substance of the device is released as the polymer degrades, shifts in the pH surrounding the polymer will be inhibited, and therefore a relatively constant pH may be achieved. In addition, because an increase in pH surrounding a polymer has been reported to increase polymer mass loss, it is expected that the usable life of devices fashioned and used according to the present invention will be prolonged. These features will thus enhance the scope of application of these and other polymer-based orthopaedic implantable devices, as well as implants employed for the delivery of pharmacologically active substances.

In a further aspect, the invention provides a method for enhancing surface porosity of an implant comprising removing at least part of an impermeable covering film or "skin" from at least one surface of the implant. The removal of part or all of the covering or "skin" may be accomplished by many different techniques. By way of example, such may be achieved by cutting away the entire skin covering of a device using a metal implement having a sharp edge of a size sufficient to remove the outer layer of the device at once. As used in the description of this method, the term "covering" is defined as an impermeable or semi-permeable skin, membrane, or film that partially or completely impedes the egress and/or ingress of substances. Removal of the "skin" or other covering from at least one surface will thus provide a simple and inexpensive method of enhancing surface porosity. The described polymeric "skin" or layer often forms at the surface of a polymeric cylinder or other device.

Alkaline substances, acidic substances and buffering agents constitute particular classes of pH-controlling substances of the invention. Many different alkaline and acidic agents, as well as salts thereof, may be employed in conjunction with the biodegradable polymer. Alkaline agents are preferably non-toxic and suitable for combination with a biodegradable polymer, such as polylactic acid, polyglycolic acid, polycaprolactone, copolymers thereof, or mixtures thereof. By way of example, alkaline agents that may be used in the practice of the invention include calcium carbonate, sodium bicarbonate, calcium hydroxyapatite, and/or salts of these substances. In addition, any combination of these and other alkaline substances or their salts may be used. In some particular embodiments, the alkaline agent is sodium bicarbonate or salts thereof.

Acidic agents may also be incorporated into a biodegradable polymer in the practice of the present invention. Of course, acidic agents that are non-toxic and amenable to mixture with a biodegradable polymer are preferred.

Where the particular polymer produces breakdown products with an overall acidic nature, alkaline pH controlling substances would be incorporated into the polymer to provide the pH regulating effect described herein. By way of example, biodegradable polymers that produce relatively acidic breakdown products include polylactic acid and polyglycolic acid. In particular embodiments, the biodegradable polymer of the claimed method is a copolymer of polylactic acid and polyglycolic acid, such as in a 50%/50% copolymer of polylactic acid and polyglycolic acid. Other biodegradable polymers that yield breakdown products with a relatively acidic character include polycaprolactone.

In these embodiments, an alkaline or alkaline releasing substance would be included with the polymer. In some embodiments, this alkaline substance is sodium bicarbonate, and is included with the polymer in an amount sufficient to achieve alkaline material release commensurate with the rate of acidic polymer degradation product. The result is an effective prevention of wide pH variation in the environment directly surrounding the polymeric device.

Where the alkaline agent of choice is sodium bicarbonate, an amount of about 1% to about 99% by volume, or in other embodiments of about 5% to about 50% by volume of the polymer issued. This alkaline substance would be included, for example, in a device comprised of a copolymer of polyglycolic acid and polylactic acid.

In other embodiments, the alkaline substance is calcium carbonate. This alkaline substance may be included with the polymer in amounts of about 1% to about 99% by volume, or in other embodiments about 5% to about 30% by volume of polymer. This would provide sufficient release of alkaline substances to offset a rapid decrease in pH in the presence of acidic polymer breakdown products.

In still other embodiments of the invention, salts of the selected alkaline substance(s) may be included with the polymer.

The alkaline, acidic, or buffering substance is to be included with the polymer in an amount and association suitable to allow the release of the material at a rate sufficient to maintain a relatively physiological pH (about 6.0 to about 8.0 pH) surrounding the implantable device.

Examples of particular alkaline substances that may be included with the devices of the invention include calcium carbonate, sodium bicarbonate, calcium hydroxyapatite, or a mixture thereof, as well as other salts of these particular substances. In one embodiment, the alkaline agent of choice is calcium carbonate. Where the selected biodegradable polymer is a copolymer of 50% glycolic acid and 50% polylactic acid, the amount of alkaline calcium carbonate to be included is between about 1% to 99% by weight, or in other embodiments about 5% to about 30% by volume of the biodegradable polymer. In still other embodiments, the alkaline substance is sodium bicarbonate.

Where the implantable device includes a biodegradable polymer that produces relatively alkaline degradation products, an acidic substance would be included to maintain a neutral pH. Such acidic agents include by way of example calcium lactate. This and other non-toxic acidic agents may be employed together with the described pH controlled implantable device in amounts sufficient to offset changes in pH caused by alkaline polymer breakdown products.

Other embodiments of the described pH controlled implantable device include a pharmacologically active agent. By way of example, such agents include anticoagulants, antibiotics, anti-inflammatories, analgesics, hormones, bioengineered cells, and the like.

In a particular embodiment, the pH controlled implantable device comprises the biodegradable polymer polylactic acid, polyglycolic acid, polycaprolactone, copolymers thereof, or mixtures thereof. Among these, copolymers of polylactic acid and polyglycolic acid are most particularly preferred.

The implantable devices of the present invention may take a variety of different forms, depending on their intended site of use. By way of example, the devices may take the form of a bone prothesis, drug delivery device, oral implant, (such as implantable tooth replacement), fracture fixation plate, pin, screw, staple, nail, scaffold for tissue growth and integration, suture, fiber, and Kirshner type biodegradable wires. However, any other implantable device that may be modified to include a biodegradable polymer having a pH controlling substance may also be made according to the present invention.

The present invention also provides a process whereby an implantable pH controlling device may be created. In one embodiment, the process comprises combining a biodegradable polymer and a pH controlling substance to form a mixture; and forming a biodegradable implantable pH-controlled device from said mixture. In particular aspects, the biodegradable polymer is a copolymer of polylactic acid and polyglycolic acid. The pH controlling substance of the device may comprise an alkaline substance, an acidic substance or a buffering agent, depending upon the acidic or alkaline nature of the polymeric breakdown products of the particular biodegradable polymer employed.

Preferably, the selected pH controlling substances are of an alkaline nature, and are included with polymers that render relatively acidic polymeric breakdown products. The most preferred alkaline substance to be employed with this class of polymers is sodium bicarbonate.

In still other embodiments, devices particularly suitable for long-term (e.g., 1-week to 2 years) implant use may be fabricated that include sufficient amounts of the biodegradable polymer and pH-controlling substances for the desired length of pH control in vivo. Such embodiments are particularly advantageous in the construction of long term implants, such as fracture fixation plates, screws, nails, pins and the like.

Because decreases in pH surrounding biodegradable polymeric devices, such as those comprised of polyglycolic acid and polylactic acid, have been associated with adverse tissue responses, the present invention may also be employed for minimizing these adverse responses at the site of an implant, as well as for enhancing the biocompatibility of a polymer implant as already described. Consequently, healing rate about the implanted device may also be enhanced. In one particular embodiment, the method for enhancing biocompatibility of a biodegradable polymer device comprises including a pH controlling substance with the biodegradable polymer of the device.

The particular amounts of the pH controlling agent (e.g., alkaline, acidic, or buffering agent), to be included with the biodegradable polymer will depend upon the particular characteristic rates of degradation, and other properties, of the specific biodegradable polymer used. Breakdown kinetics for biodegradable polymers currently employed are well known to those of ordinary skill in the art, as noted in Gilding et al. (1979).[11] This reference is specifically incorporated herein by reference for its teachings of polymer production and polymer characteristics.

This information well known to those of skill in the art, together with the teachings of the present invention, provide sufficient direction to the artisan of ordinary skill regarding the application and use of the present invention with many different polymers. Together with the information provided in the present disclosure, specially tailored polymeric devices may be fabricated that include appropriate amounts of an alkaline substance, acidic substance, or buffering agent, sufficient to achieve a calculated pH maintaining effect over a desired and therapeutically useful period of time.

These and other aspects of the invention are more fully to be appreciated in light of the detailed description of the preferred embodiments and figures.

DETAILED DESCRIPTION OF THE PREFERRED EMBODIMENTS

Figure 1A:
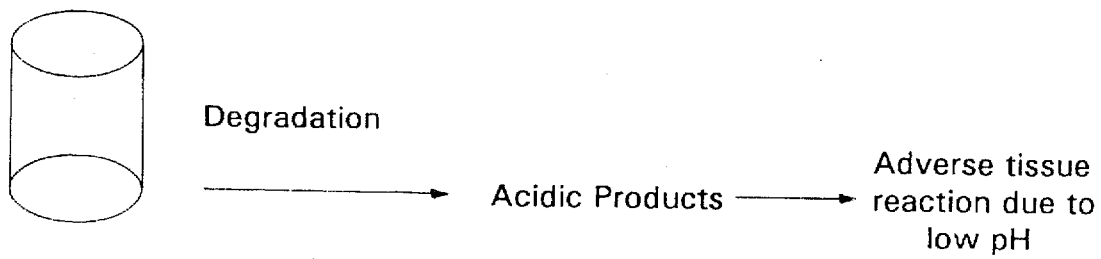
FIG. 1A and FIG. 1B—Schematic flow chart of biodegradable PLA-PGA polymer implant without an alkaline (basic) substance (FIG. 1A) and with an alkaline (basic) substance (FIG. 1B).
Figure 1B:
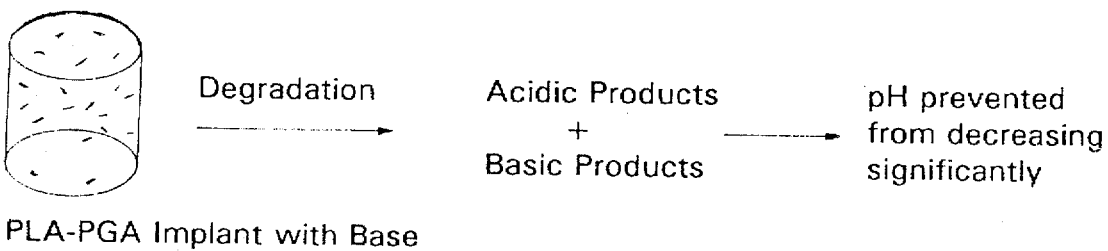

The present invention provides both devices and methods of employing said devices for regulating pH. This is accomplished by preparing a mixture of an alkaline, acidic or buffering substance with a biodegradable polymer, and preparing an implantable device with the mixture. The mixture may also include a pharmacologically active agent.

The invention also provides methods for preparing such devices, as well as methods of using these devices to enhance the biocompatibility of an implantable device over clinically useful periods of time.

These and other aspects of the invention will be illustrated in the following examples. However, these examples are intended to illustrate specific embodiments of the present invention only. Those skilled in this field will recognize that modifications could be made to the disclosed methods and that other applications would remain within the scope of the present invention.

EXAMPLE 1

Fabrication of Polymeric Implants

The present example describes the incorporation of materials with a basic nature (pH>7.0) in implants fabricated from polymers or copolymers belonging to the family of polylactic and polyglycolic acids. This idea can be implemented in several ways, one of which is described below:

A solution of a 50:50 PLA-PGA copolymer was prepared in acetone. Alternatively, methylene chloride or chloroform may be used to prepare the polymer. The polymer was then precipitated in ethanol. Alternatively, the polymer may be precipitated in methanol or other alcohol. The precipitate was extracted and the basic salt (30 percent by volume with respect to polymer) is then rolled/kneaded into the polymer. The polymer was then packed into a mold and dried under heat and vacuum to yield the implant.

Upon degradation in vivo or in vitro, the PLA and PGA polymers in the implant will release lactic and glycolic acids. Simultaneously, the basic salt will dissolve in the surrounding media and neutralize the acids in the vicinity of the implants.

In these implants, the pH-controlling material is evenly distributed throughout the device. Methods for preparing these implants constitute still another aspect of the invention.

EXAMPLE 2

In Vitro Regulation of pH

The present example provides an in vitro study offset of changes (particularly decreases) in pH surrounding a biodegradable polymer provided by incorporation of salts with a basic nature within the implants.

MATERIALS AND METHODS

Biodegradable implants were fabricated using a 50:50 PLA-PGA copolymer with inherent viscosity of 0.71 dl/gm and weight average molecular weight of 53 kD. These implants were divided into 4 groups: a control group, and 3 test groups corresponding to 3 basic salts: calcium carbonate (CC), sodium bicarbonate (SB), and calcium hydroxyapatite (CH). Each of these groups were further subdivided into four sets corresponding to test periods of 0, 3, 6, and 9 weeks. For fabrication the polymer was dissolved in acetone and precipitated in ethanol. Next, the reagent quality salts (30% v/v) were added to the gummy polymer and the polymer-salt composite was packed into molds, and placed under 25 mTorr vacuum at room temperature for curing. The control specimens did not contain any salts.

Prior to testing, the mass of each specimen was recorded. Next, each specimen of the 3, 6, and 9 week sets was immersed in 10 ml of distilled water and maintained at 37° C. The pH of the water was monitored every 2 days. At the end of each test period, the specimens were removed, dried in a vacuum for 72 hours and then analyzed for changes in mass, molecular weight, mechanical properties, and surface morphology. The molecular weight of the polymer was estimated using gel permeation chromatography. The mechanical properties of the specimens were measured under creep conditions using an automated indentation apparatus.

RESULTS

Figure 2:
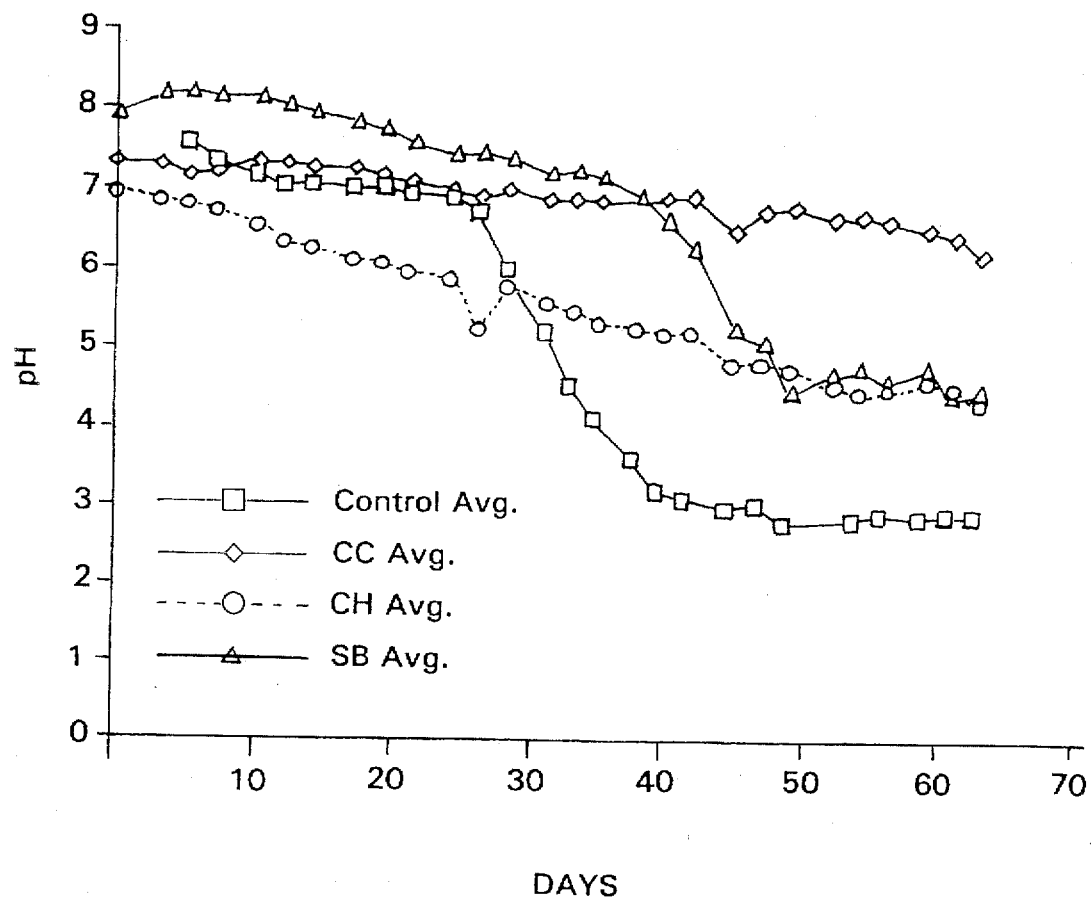
FIG. 2—Change of pH as a function of degradation time: □=control (no alkaline substance); ◇=calcium carbonate (CC); ○=calcium hydroxyapatite (CH); and a △=sodium bicarbonate.
Figure 3:
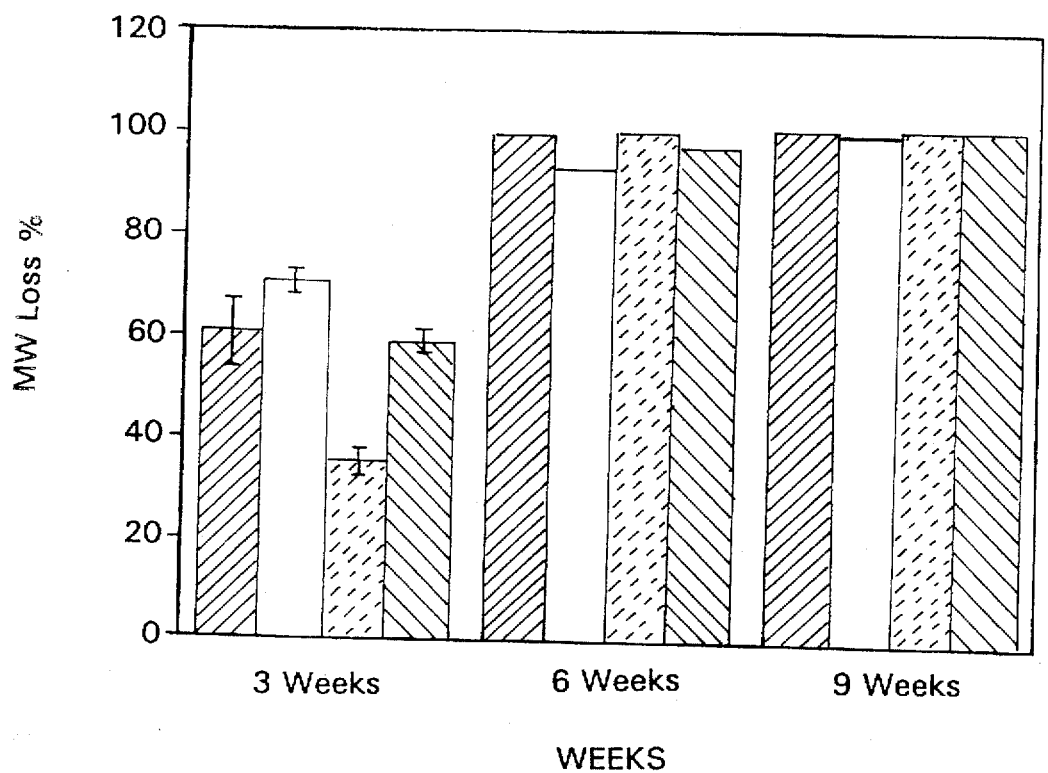
FIG. 3—Loss in molecular weight of implants as a function of time. Con=control; CC=calcium carbonate; CH=calcium hydroxyapatite; SB=sodium bicarbonate.

The pH of the water of the control specimens remained relatively constant up to 3.5 weeks followed by a rapid decrease until approximately 7 weeks (FIG. 2). The SB specimens exhibited only a small decrease in pH up to 5.5 weeks. However, between 5.5 and 7 weeks there was a significant decrease in pH followed by a relatively constant value thereafter. The CH specimens displayed a linear decrease in pH up to 9 weeks. The CC specimens exhibited an approximately linear but small decrease in pH over the entire test period.

Figure 4:
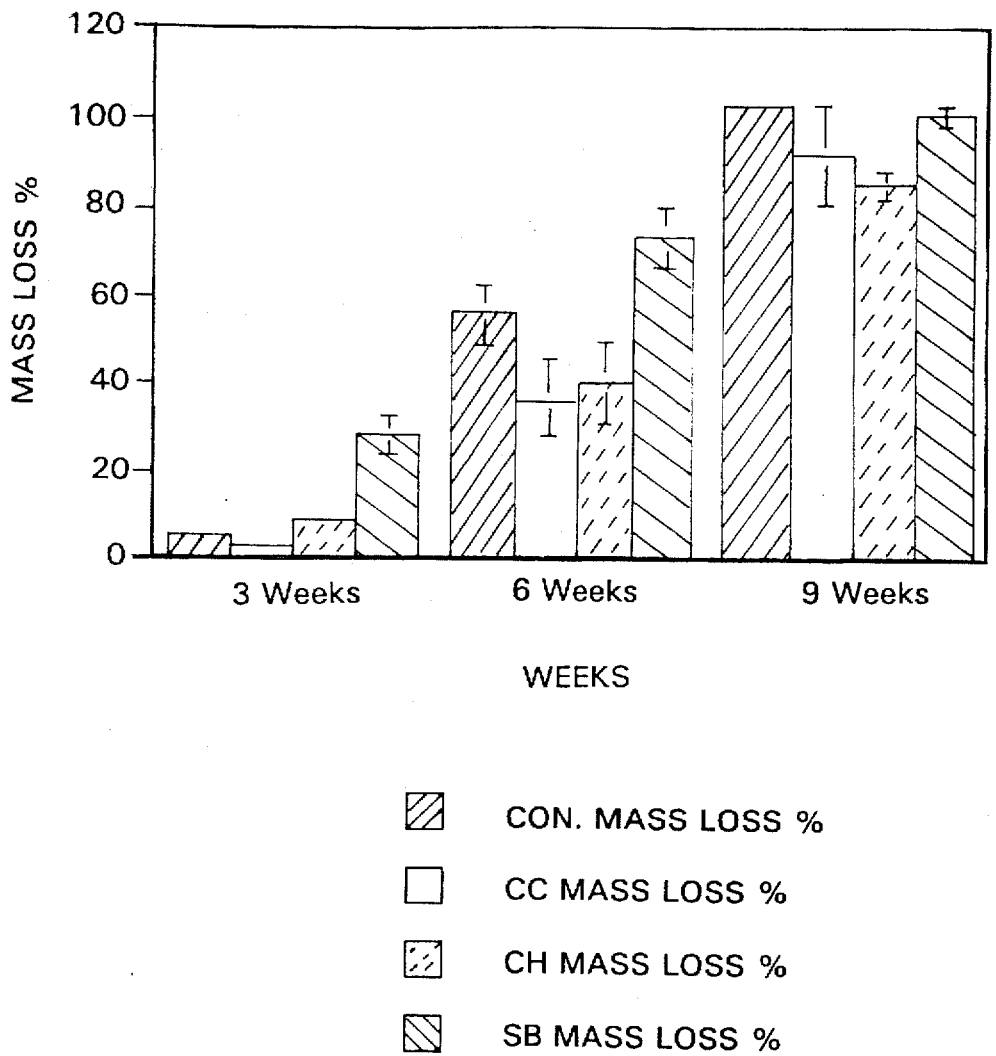
FIG. 4—Mass loss in wt% between various constructs at 3 weeks, 6 weeks and 9 weeks.
Figure 5:
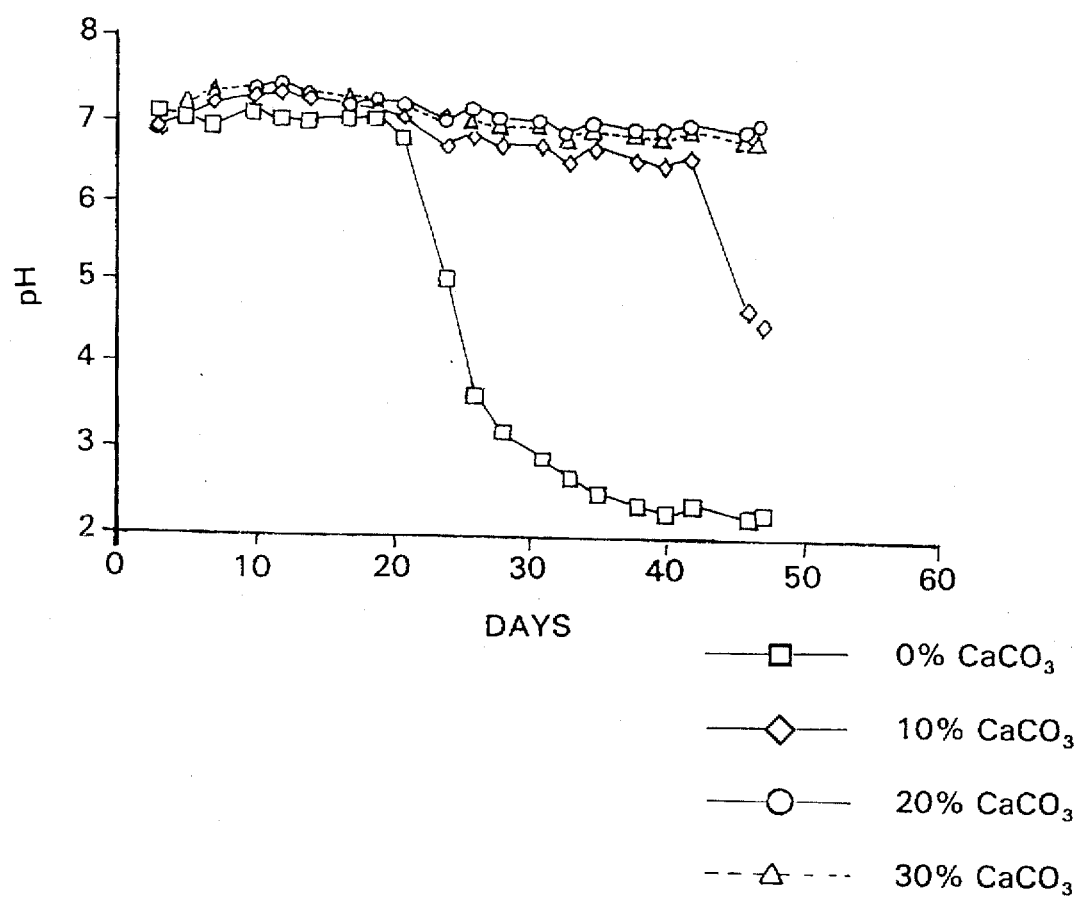
FIG. 5—Polymer implants of 50/50 PLA-PGA and 0% (□), 10% (◇), 20% (○), 30% (△) $CaCO_3$.

As shown in Table I, the SB specimens exhibited the maximum mass loss at 3 weeks. However, at 9 weeks the difference between the control and SB specimens was not significant (FIG. 4). All the sets exhibited virtually a 100% decrease in molecular weight at 9 weeks even though they underwent different degrees of loss at 3 weeks. The control and CH specimens exhibited an increase in stiffness at 3 weeks. However, the stiffness of SB specimens decreased over this same period of time.

Based on gross morphology observations, SB specimens exhibited significant swelling compared to control specimens. Significant swelling was also observed in CC specimens.

TABLE I

Percent Loss in Mass and Molecular Weight

| Week | CC | CH | SB | Control |
|---|---|---|---|---|
| 3 | 2.24 ± 0.6/ | 8.28 ± 1.6/ | 27.7 ± 4.2/ | 4.84 ± 0.13/ |
|  | 7.0.2 ± 4.9 | 34.9 ± 2.6 | 58.3 ± 2.4 | 60.64 ± 6.28 |
| 6 | 34.7 ± 9.6/ | 78.7 ± 9.2/ | 71.7 ± 6.4/ | 55.05 ± 6.39/ |
|  | 92.1 ± 1.5 | 99 ± 0.1 | 95.8 ± 1.1 | 99.0 |
| 9 | 88.9 ± 10/ | 82.5 ± 2.8/ | 97.4 ± 1.9/ | 99.5 ± 0.01/ |
|  | 100 | 99 ± 0.1 | 100 | 99.0 ± 0.02 |

% mass loss/% molecular weight loss; mean ± s.d.

The results demonstrated that all 3 salts investigated in this study were successful in controlling the decrease in pH due to the acidic degradation products of the copolymer. At 9 weeks the CC group exhibited an average pH of 6.3 compared to 3.0 for the control group. Implants containing CC maintained the pH value between 7.4–6.3 throughout the degradation process of the PLA-PGA copolymer until complete degradation was achieved. Implants with CH and SB controlled the pH values between 6.9–4.3 and 8.2–4.5 respectively. Thus, the results of this study show that a decrease in pH in the vicinity of PLA-PGA implants can be effectively controlled by incorporating basic salts. Thus, the deleterious effects of such implants reported by other researchers related to a decrease in pH may be offset using the presently disclosed techniques.

EXAMPLE 3

Process for Enhancing Surface Porosity of a Biodegradable pH-Controlling Device

It is well known that the fabrication process for preparing porous polymeric devices (e.g., PLA-PGA) often results in the formation of a relatively impermeable and non-porous outer covering or "skin". While this "skin" does not destroy the internally porous structure, it creates a problem because it impedes to varying degrees the passage of fluids and other substances into and out of the porous internal structure of the polymer. Thus, it is desirable to devise a fabrication process that achieves a uniformly porous and permeable implant. According to the presently described technique, enhanced surface porosity may be achieved by removing all or a portion of the non-porous "skin".

A new method to increase the surface porosity of porous devices treated or created with polymeric materials has been designed. This is particularly important in the context of the present invention, as the biodegradable polymeric devices will more readily adapt to and control against pH shifts in the environment where surface porosity is maximized.

In the present example, a 50:50 PLA-PGA porous implant was prepared as defined in example 1. The polymer included an alkaline pH controlling substance, sodium bicarbonate. In the formation of such devices, a "skin" forms at the polymer surface. Using a mechanical device devised by the inventors, a quick and consistent removal of the skin was achieved. In one embodiment, the mechanical device is a circular punch with a sharp cutting edge. All of the skin of a rod-like polymeric cylinder was effectively removed by slicing the skin away.

The surface porosity of the polymeric implant prepared according to the present invention is dramatically improved by removing the outer layer, or skin, from the polymer implant. The porous outer surface will result in enhanced ingress of fluids into the implant, thus resulting in better release of the buffering agents.

It is also expected that body fluids (e.g., vascular supplies, marrow, synovial fluid) will be able to enter the implant much more expediently and thus provide the repair sites with migrating cells (e.g., mesenchymal stem cells, chondrocytes, osteoblasts) or nutrients necessary for tissue ingrowth into the porous implant.

EXAMPLE 4

Layering Technique Alkaline Agent Release from a Polymer Coated Implant

In some biodegradable devices, depending on the polymer used for fabrication, the release of acidic by-products occurs in significant quantities only after an initial incubation period. It would be preferable to provide a mechanism for the release of an alkaline agent(s) in an amount that would prevent sudden changes in pH that would occur as a consequence, such as through the release of matching amounts of said alkaline agent(s) at the same or similar rates. Such would provide an implantable device having pH control over a clinically useful period of time.

In order to achieve an appropriate release rate of an alkaline agent, the alkaline agents may be incorporated in the implant in layers. For example, each layer of alkaline agent would be overlaid by a layer of the biodegradable polymer, alternating alkaline agent layer, polymer layer, etc. As each layer degrades, the alkaline or other pH-controlling substance is released, thus controlling against an overly acidic pH surrounding the implant over an extended period of time.

Any variety of configurations of the layered polymeric implant may be created using this technique and tailored for the particular application desired. For example, a base amount of a pH controlling substance may be included in polymeric layers closest the core of an implant, with succeeding layers containing either progressively lower or higher amounts of the pH controlling substance.

Although the present invention has been described in some detail by way of illustration and example for purposes of clarity and understanding, it will be obvious that certain changes and modifications may be practiced within the scope of the claims.

The references listed below are incorporated herein by reference to the extent they supplement, explain, provide a background for or teach methodology, techniques and/or compositions employed herein.

REFERENCES

1. Bostman et al. (1987), *J. Bone. J. Surgery*, 69-B: 615–619.
2. Suganuma, J. and Alexander, H. (1993), *J. Appl. Biomaterials*, 4: 13–27.
3. Daniels et al. (1992), *Proc. Orthop. Res. Soc.*, pg. 88.
4. Taylor et al. (1994), "Six Bioadsorbaliler Polymers/in Vitro Acute Toxicity of Accumulated Degradated Materials," *J. Appl. 'd Bio. Materials*, 5:151–157.
5. Tencer et al. (1986), "Bone ingrowth into Polymer Coated Porous Synthetic Coralline Hydroxyapatite," IEEE/ *Engineering in Med. And Biol. Soc.*, Annual Conference, pp. 1668–1671.
6. Fong, J. W., U.S. Pat. No. 4,479,911, Oct. 30, 1984, "Process for Preparation of Microspheres and Modification of Release Rate of Core Material; Mixing Alkalinity Agent with Polymer-Core-Solvent System."
7. Kampner S.L., U.S. Pat. No. 4,990,161, (1991) "Bone Implant with Resorbable Stem Has Biodegradable Anchor with Exterior Surface to Engage Interior of Bone Canal."
8. Allemann et al. (1993), "In vitro Extended-release Properties of Drug-loaded Poly (DL-lactic acid) Nanoparticles Produced by a Salting-out Procedure," *Pharm. Res.*, 10:12.
9. Younes et al. (1988), "Biodegradable PELA Block Copolymers: in vitro Degradation and Tissue Reaction," *Bimater. Artif. Cells Artif. Organs*, 16 (4): 705–719.
10. Mariette et al. (1993), "Release of the GRF29NH2 Analog of Human GRF44NH2 from a PLA/GA Matrix," *J. Control Release*, 24 (1–3): 237–246.
11. Vasenius et al. (1992), "Do Intramedullary Rods of Self-reinforced Poly-L-lactide or Poly-DL/L-lactide Cause Lactic Acid Acidosis in Rabbits?"*Clin. Mater.* 10(4):213–218.
12. Gilding and Reed (1979), "Biodegradable polymers for use in surgery-polyglycolic/poly (lactic acid) homo- and copolymers," *Polymer*, 20:1459–1464.

What is claimed is:

1. A method for preventing changes in pH surrounding an implantable device comprising:

placing a device comprising a pH-controlling substance, and a biodegradable polymer in an environment that degrades the biodegradable polymer; wherein when said polymer produces acidic breakdown products, said pH-controlling substance is an alkaline substance present in an amount between about 5% and about 30% by volume based on the volume of the polymer, sufficient to achieve alkaline material release commensurate with the rate of acidic polymer degradation product.

2. The method of claim 1 wherein the pH controlling substance is an alkaline substance, acidic substance or a buffering agent.

3. The method of claim 1 wherein the biodegradable polymer is polylactic acid, polyglycolic acid, polycaprolactone, a copolymer thereof, or a mixture thereof.

4. The method of claim 1 wherein the alkaline substance is calcium carbonate, sodium bicarbonate, calcium hydroxyapatite, salts thereof, or a mixture thereof.

5. The method of claim 1 wherein the biodegradable polymer mixture includes a pharmacologically active agent.

6. The method of claim 1 wherein the biodegradable polymer is a copolymer of polylactic acid and polyglycolic acid.

7. The method of claim 6 wherein the biodegradable polymer is a 50%:50% polylactic acid-polyglycolic acid copolymer.

8. The method of claim 1 wherein the pH controlling substance is released at a rate commensurate with the rate of biodegradable polymer degradation.

9. The method of claim 7 wherein the pH controlling substance is an alkaline substance.

10. The method of claim 1 wherein the pH-controlling substance is calcium carbonate included in an amount of about 5% to about 30% by volume of the polymer.

11. The method of claim 1 wherein the pH controlling substance is released at a rate sufficient to maintain a pH of between about 6.0 and about 8.0 surrounding the implantable device.

12. A biodegradable pH-controlled device comprising a biodegradable polymer and a pH-controlling substance, wherein the pH-controlling substance is dispersed in the biodegradable polymer; and wherein when said polymer produces acidic breakdown products, said pH-controlling substance is an alkaline substance present in an amount between about 5% and about 30% by volume based on the volume of the polymer, sufficient to achieve alkaline material release commensurate with the rate of acidic polymer degradation product.

13. The biodegradable pH-controlled device of claim 12 prepared by a process of:

combining a biodegradable polymer and a pH controlling substance to form a mixture;

forming a biodegradable pH-controlled device from said mixture.

14. The biodegradable pH-controlled device of claim 12 wherein at least part of a polymer surface film is removed from at least one surface.

15. The device of claim 12 wherein the pH-controlled device is formed by extrusion molding, die casting, solution gel casting, precipitation casting or compression molding.

16. The biodegradable pH-controlled device of claim 12 wherein said pH controlling substance is calcium carbonate present in an amount between about 5% and about 30% by volume of the polymer.

17. A method for preventing changes in pH surrounding an implantable device comprising:

placing a device comprising sodium bicarbonate and a biodegradable polymer in an environment that degrades the biodegradable polymer.

18. The method of claim 17 wherein the biodegradable polymer is a 50%50% polylactic acid-polyglycolic acid copolymer and the sodium bicarbonate is included in an amount of about 1% to about 50% by volume of the copolymer.

19. The method of claim 18 wherein the sodium bicarbonate is included in an amount of about 5% to about 30% by volume of the copolymer.

* * * * *